United States Patent [19]

Jones et al.

[11] Patent Number: 4,786,372
[45] Date of Patent: Nov. 22, 1988

[54] ELECTROCHEMICAL MEASURING

[75] Inventors: Ronald L. Jones, Newton, N.H.; Alan D. Cormier, Newburyport, Mass.; Melvin S. Weinberg, Nashua, N.H.

[73] Assignee: Amdev, Inc., Danvers, Mass.

[21] Appl. No.: 757,648

[22] Filed: Jul. 22, 1985

[51] Int. Cl.⁴ ............................................. G01N 27/46
[52] U.S. Cl. ................................. 204/1 T; 204/400; 204/409; 204/416
[58] Field of Search ......... 204/1 T, 400, 409, 416–419

[56] References Cited

U.S. PATENT DOCUMENTS

| | | | |
|---|---|---|---|
| 3,556,950 | 1/1971 | Dahmr | 204/1 T |
| 3,840,438 | 10/1974 | Ast et al. | 254/435 |
| 4,202,747 | 5/1980 | Buzza et al. | 204/411 |
| 4,218,197 | 8/1980 | Meyer et al. | 204/411 |
| 4,236,988 | 12/1980 | Suzuki et al. | 204/1 T |
| 4,253,897 | 3/1981 | Matson et al. | 204/1 T |
| 4,283,262 | 8/1981 | Cormier et al. | 204/411 |
| 4,424,276 | 1/1984 | Clark et al. | 204/1 T |
| 4,627,893 | 12/1986 | Cormier et al. | 204/401 |

Primary Examiner—T. Tung
Attorney, Agent, or Firm—Wolf, Greenfield & Sacks

[57] ABSTRACT

A fluid arrangement for analyzing a fluid sample using an electrochemical measuring apparatus having an analyzing device with an inlet port and an outlet port, the outlet port connecting to an outlet tube, the inlet port connecting to an inlet tube having a sample fluid receiving end, and the inlet tube connecting at a junction along its length to one end of a fluid supply tube, which fluid supply tube is connected at its opposite end to at least one fluid source containing a fluid. In a first mode, the fluid from the supply source flows through the fluid supply tube to the junction and the fluid then flows simultaneously in a proximal direction and a distal direction within the inlet tube from the junction, and in a second mode, a fluid sample is drawn through the inlet tube past the junction and into the analyzing module.

23 Claims, 8 Drawing Sheets

ELECTROCHEMICAL MEASURING

This invention relates generally to the analysis of fluid samples and more particularly to a fluid arrangement for calibrating, introducing a sample into, and washing the analyzing module of an electrochemical measuring apparatus.

Electrochemical measuring apparatus are commonly used to determine constituents of a fluid sample of small volume, for example, a blood serum sample. Typically, analyzing modules are interconnected with conventional electronics, pumping and flow meters and the like. The analyzing module measures electromotive force between a reference electrode and an electrode mounted beneath a membrane over which a fluid is passed to determine, for example, the ionic content of the fluid.

The accuracy of an electrochemical measuring apparatus can be critical where the apparatus is used for analyzing a blood sample to provide diagnostic information or to control a life support device. The speed of an electrochemical measuring apparatus can also be critical in these contexts, but is especially critical regarding the economics of large scale laboratory analysis of multiple blood samples. The fluid arrangements for electrochemical measuring apparatus currently used can have limitations in accuracy and speed of operation.

Typically, analyzing modules include an inlet port and an outlet port, which ports connect with the module analyzing chamber. A tube usually connects to the inlet port for introducing fluids into the chamber. Another tube connects to the outlet port for carrying away fluids exiting from the chamber. An aspirator pump is connected to this outlet tube to cause fluids to be drawn through the inlet tube and analyzing chamber.

There are a plurality of known general fluid arrangements used with various electrochemical analyzing apparatus. Examples of these are the IL501 and Il502, Instrumentation Laboratories Lexington, Mass., U.S.A., the ORION 1020, Orion Research, Cambridge, Mass., U.S.A., and the Nova 1, Nova Biomedical, Waltham, Mass. U.S.A. In some fluid arrangements, the apparatus includes a valve between the point where the sample is introduced into the inlet tube (sample-receiving end) and the module inlet port. Such a valve can trap contaminants which may be picked up as a sample passes through the valve, rendering inaccurate the ultra-sensitive reading of the analyzing module. The valve is also a mechanical part that may degrade or malfunction, that adds additional expense and that increases maintanance. These apparatus also commonly operate by introduction of a wash solution to the sample-receiving end to wash the tube between this point and the valve once a sample has passed through. This step can add substantially to the total time required to test multiple samples, especially where this step is accomplished manually.

In other electrochemical measuring apparatus the fluid arrangement includes a second pump which can cause a wash solution or calibrant to flow through the module in reverse direction, that is, first into the module outlet port, through the module chamber, exiting the module through the module inlet port and ultimately passing through the inlet tube. While this arrangement sometimes eliminates potentially contaminating valves, it contaminates the washing/calibrating fluid, thus rendering it useless for calibration subsequent to washing.

Many modules are designed to operate properly only with unidirectional flow. For example, a module may have a series of chambers, the last having a reference electrode. During flow across the membrane, potassium ions are released which, if flowing in the proper direction, exit the module. If the flow is reversed, these potassium ions are continually introduced into the earlier chambers in series. These ions are contaminants which can cause an erroneous measurement when a sample is passed through. It is common in many other arrangements to calibrate the module under a different set of conditions than when testing a sample in the module. In general, analyzing modules are highly sensitive to pressure, flow rate, electric potential and other variables. Thus, calibrating a module under a different set of conditions than testing a sample can lead to an erroneous measurement.

Still other arrangements, while eliminating valves and reverse flow over the analyzing module, require mechanical manipulation of the inlet tube for introducing the sample and the various washing and calibrating fluids into the analyzing module. Such manipulation increases the time for the analyzing cycle, requires increased parts maintenance and cost and reduces reliability. Finally, the inlet tube in virtually all known arrangements follows a sinuous path further adding to the time for operating the apparatus and enhancing the risk of contamination and erroneous measurement.

SUMMARY OF THE INVENTION

It is an object of this invention to provide a means and method for rapidly and efficiently determining ionic concentration of various ions in fluids, as for example in blood serum.

Another object of this invention is to provide a means and method for accurately determining the ionic concentration of various ions in fluids, as for example in blood serum.

Still another object of the invention is to provide a fluid system useful with many analyzing modules for accomplishing the preceding objects.

Still another object of the invention is to provide a fluid arrangement for electrochemical analyzing apparatus which employs a short straight tube for introducing the sample into the analyzing module.

It is still another object of the invention to provide a fluid arrangement for an electrochemical measuring apparatus which introduces the sample into the analyzing module without causing the sample to pass through any valves.

According to the invention, an electrochemical measuring apparatus is provided with an analyzing device with an inlet port and an outlet port, the outlet port connecting to an outlet tube, and the inlet port connecting to an inlet tube having a sample-receiving end. The inlet tube connects by a junction at a point along its length to one end of a fluid supply tube, this fluid-supplying tube being connected at its opposite end to at least one fluid source. A first pumping means for advancing the fluid from the fluid source to the juncion is connected at a point along the length of the fluid supply tube. A second pumping means is connected at a point along the length of the outlet tube for execting a force to continuously draw the fluid proximally through the inlet tube at the junction. This force draws at a rate that is slower than the rate that the fluid advances into the junction such that the excess fluid passes distally in the inlet table toward the sample receiving end of the inlet tube. Applicants' fluid arrangement functions without the use of any accessory tube closing means. Also according to applicants' invention, the first pumping means is reversed to create an air bubble in the fluid supply tube at the junction. Then, the second pumping means exerts a drawing force to draw a sample into the sample-receiving end of the inlet tube and through the inlet tube past the junction and into the analyzing device without the sample passing through any valves that might contaminate the sample. According to the method of applicants' invention, a fluid is advanced by the first pumping means to the junction at the inlet tube and the fluid is drawn through the inlet tube to the analyzing device by a drawing force exerted by the second pumping means. This drawing force occurs at a rate that is slower than the rate that the fluid advances into the junction so that the excess fluid passes distally from the junction toward the sample-receiving end of the inlet tube. In this manner, a fluid can be introduced in a continuous flow into the analyzing device via the fluid supply tube without using any valves and thereby reducing the chance of contmination.

Also according to the method of applicants' invention, a fluid is drawn proximally through the inlet tube past the junction and to the analyzing device. This is accomplished by creating and maintaining an air bubble in the fluid supply tube at the junction putting the sample receiving end of the inlet tube in contact with a fluid sample, and exit in a force to draw the fluid sample proximally through the inlet tube.

The analyzing module and the inlet tube can be washed and the analyzing module calibrated without the need for any valve. The washing action can be further enhanced by turning the first pumping means on and off to create air spaces which pass through and scrub the analyzing device.

Applicants' inlet tube is short and straight to further enhance the speed for operating applicants' invention and to further enhance the accuracy of measurement in applicants' invention. Finally, the analysis of the calibant and the analysis of the sample occur under exactly the same flow conditions and accuracy in measurement is further enhanced.

It is a feature of this invention that many problems of the prior art devices can be avoided with speed and accuracy of measurement enhanced.

BRIEF DESCRIPTION OF THE DRAWINGS

A preferred embodiment of the invention will now be described by way of example with reference to the accompanying drawings illustrating different modes of operation of a preferred apparatus in accordance with the methods of this invention in which.

DETAILED DESCRIPTION OF THE INVENTION

Figure 1:
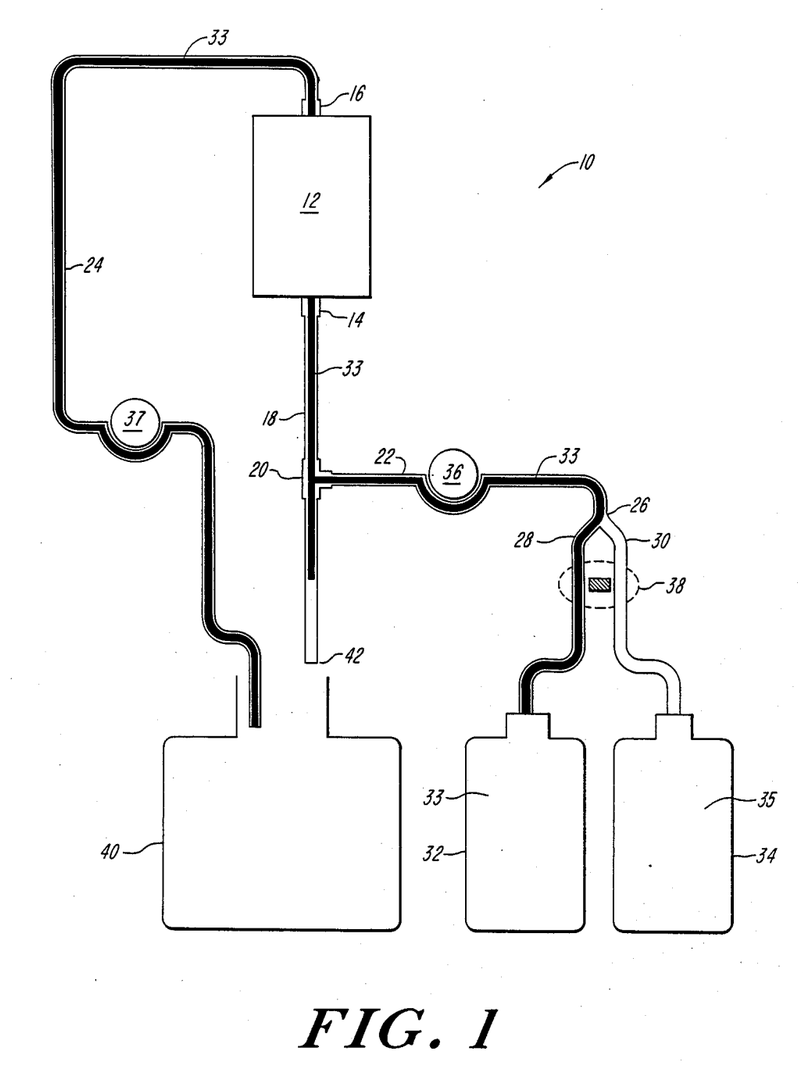
FIG. 1 is a schematic view of a resting mode of operation of the fluid arrangement.

FIG. 1 illustrates schematically the applicants' invention in a resting mode of operation. An electrochemical analyzing apparatus fluid arrangement 10 includes an electrode-analyzing module 12 having an inlet port 14 and an outlet port 16. Many such electrode-analyzing modules are commercially available, although it is preferable to use a module supplied by AMDEV, Inc., Haverhill, Mass. U.S.A., the AMDEV 2 Channel, Part No. 85001, when measuring sodium and potassium concentrations. It is also possible to use this fluid arrangement with systems other than electrochemical apparatus in which case other appropriate analyzing devices would be required. In a preferred embodiment, this analyzing module may be connected with conventional electronics for converting the flow generating analog signal of the module into a digital signal displayed, for example, on a liquid crystal display.

The inlet port 14 is connected to an inlet tube 18, which is in the preferred embodiment a short straight tube having I.D. of approximately 0.030 inches. At a point along the length of the inlet tube 18, there is a "T" junction 20 which connects the inlet tube to a fluid supply tube 22. The fluid supply tube 22 bifurcates at supply tube junction 26 forming a first calibrant supply tube 28 and a second calibrant supply tube 30. The first calibrant supply tube is connected to first calibrant supply source 32 and the second calibrant supply tube 30 is connected to the second calibrant supply source 34. The first calibrant supply source 32 contains first calibrant 33 and the second calibrant supply source 34 contains second calibrant 35. A first peristaltic pump 36 is connected to the fluid supply tube 22 for advancing calibrant fluid from the first or second calibrant supply source 32, 34 through the fluid supply tube 22 to the junction 20. Suitable peristaltic pumps are generally commercially available although it is preferable to use the noiseless peristaltic pump sold by AMDEV, Inc., Part No. 85003. A pinch valve 38 controls which calibrant supply source is accessed. For example, when the pinch valve closes the second calibrant supply tube 30, the pump will advance first calibrant 33 from the first calibrant supply source only. Again, suitable pinch valves are generally commercially available, although applicants prefer a pinch valve sold by Bio-Chem Valve Corp., East Hanover, N.J., U.S.A. The first peristaltic pump 36 may also pump the calibrant away from the junction 20 toward the calibrant supply sources 32, 34.

The analyzing electrode module 12 is connected at its outlet port 16 to an outlet tube 24. At a point along the length of this outlet tube 24, a second peristaltic pump 37 is connected.

In the resting mode of applicants' invention, the first calibrant 33 occupies the outlet tube 24, the analyzing electrode module 12, the fluid supply tube 22, the calibrant supply tube 28, and a portion of the inlet tube 18. The portion of inlet tube 18, not occupied with first calibrant 33, is instead occupied by air. Pinch valve 38 is applied to second calibrant supply tube 30 to permit the flow of the first calibrant 33.

Figure 2A:
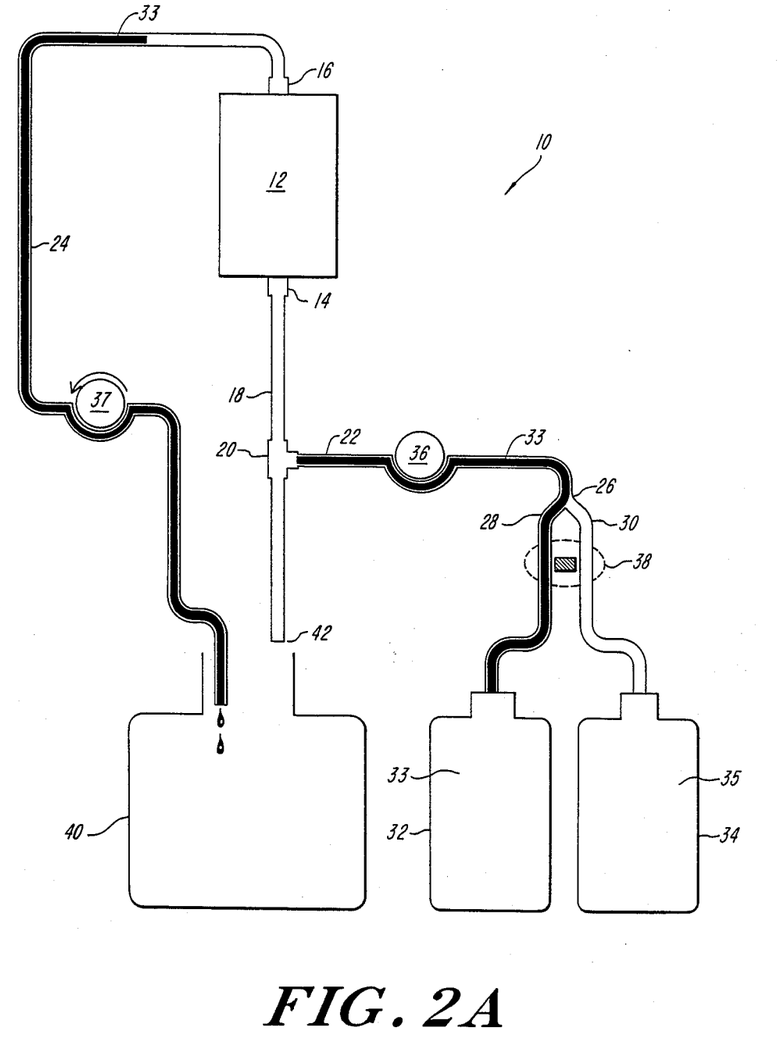
FIGS. 2A and 2B show schematic views of part of the sample introducing mode of the fluid arrangement.
Figure 2B:
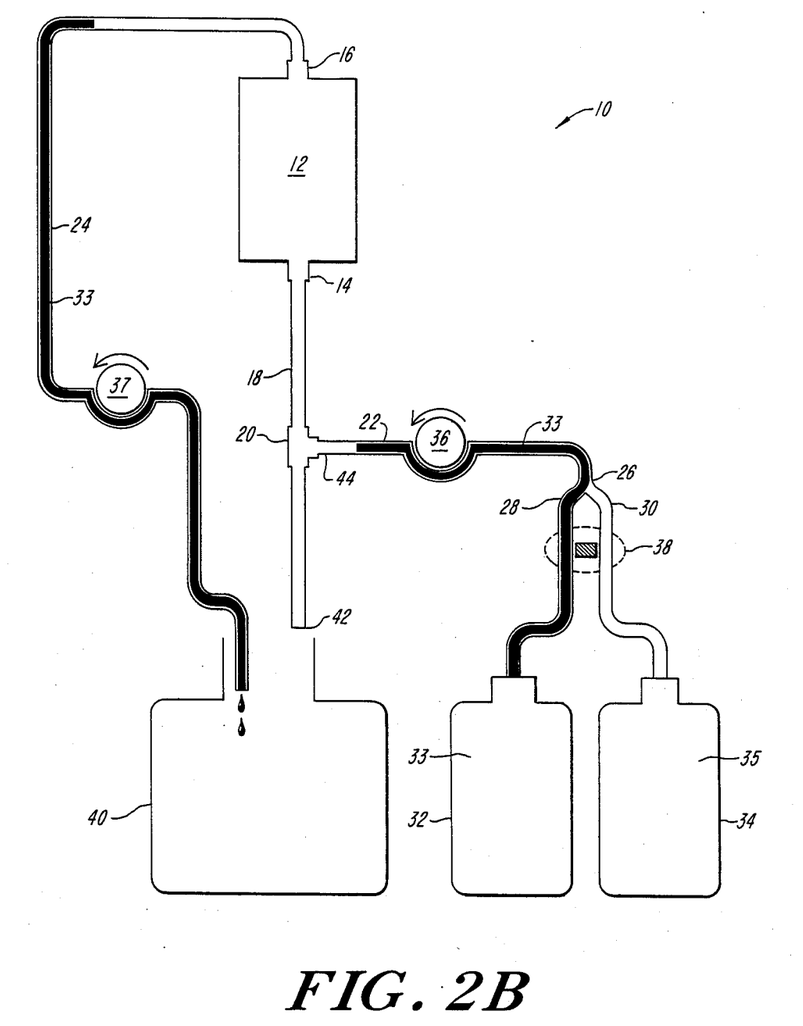
Figure 3:
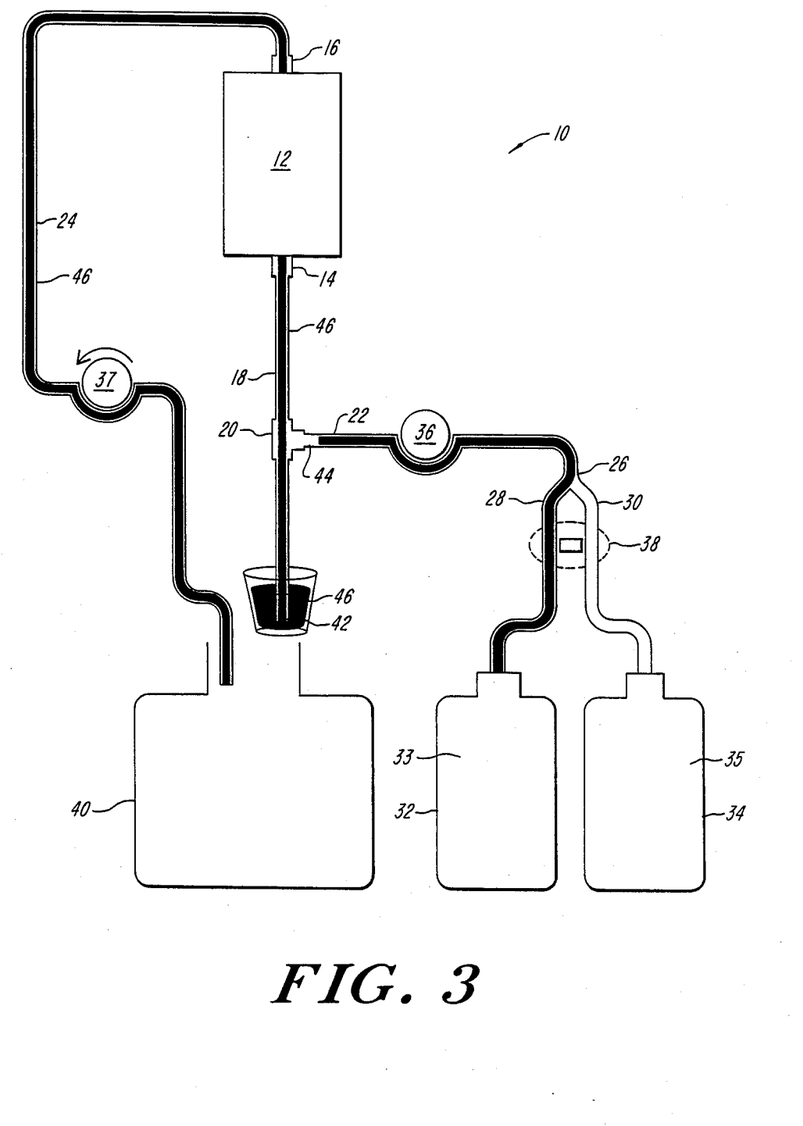
FIG. 3 is a schematic view of a part of the sample introducing mode of operation of the fluid arrangement.

A sample introducing mode of applicants' invention is shown in FIGS. 2A, 2B and 3. In FIG. 2A, the second peristaltic pump 37 is turned on causing flow in the direction of the arrow. In this manner, the first calibrant 33 remaining in the inlet tube 18 will be drawn through the analyzing electrode module 12 and will be replaced by air. In FIG. 2B, the first peristaltic pump 36 is reversed a quarter turn to produce an air gap 44 in the fluid supply tube 22 at the junction 20. Then, as illustrated in FIG. 3, a sample fluid 46 is applied to the sample-receiving end 42 of inlet tube 18 and is drawn proximally to the analyzing electrode module 12 by the action of the second peristaltic pump 37. The air gap 44 in the fluid supply tube 22 acts as a barrier preventing the sample fluid 46 from being contaminated by the first calibrant 33 in the fluid supply tube 22 as the sample fluid 46 passes through the inlet tube 18.

Figure 4:
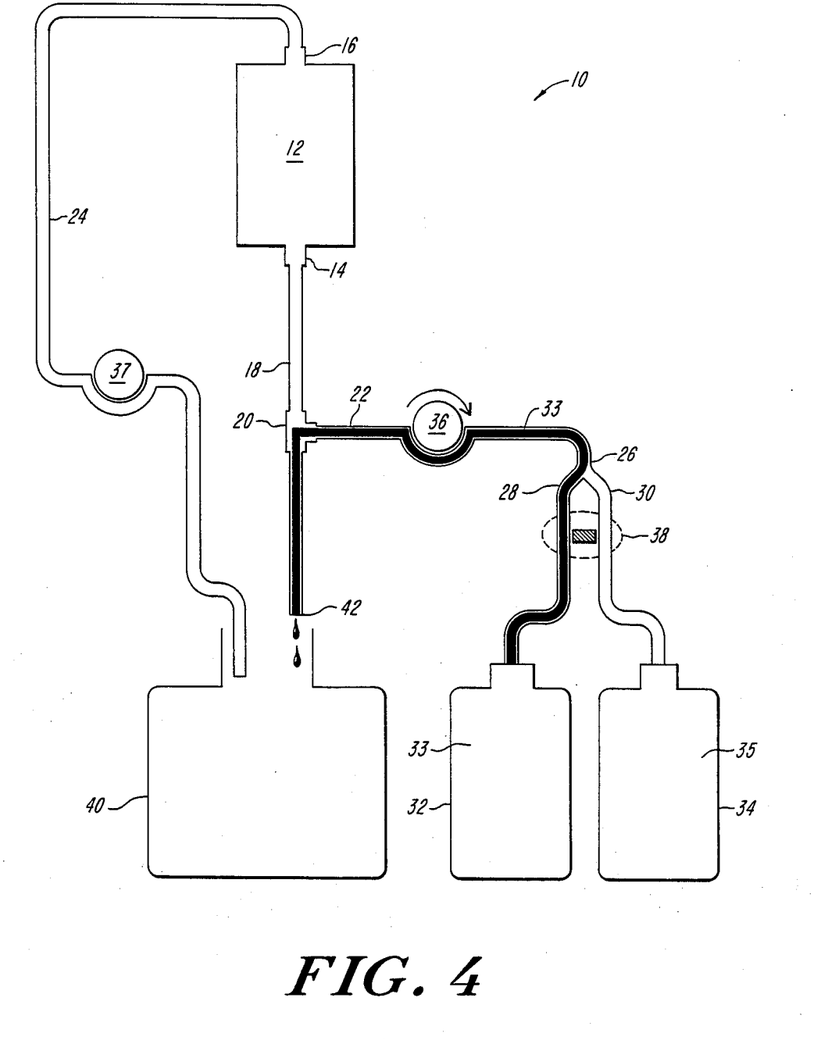
FIG. 4 is a schematic view of a first washing mode of operation of the fluid arrangement.

FIG. 4 illustrates a first washing mode of operation of applicants' invention. In this first washing mode, the second peristaltic pump 37 is turned off and the first peristaltic pump is turned on to advance the first calibrant 33 to the junction 20 and then distally from the analyzing electrode module 12 through the inlet tube 18 and out the sample-receiving end 42. In this manner, the portion of the inlet tube 18 between the junction 20 and the sample-receiving end 42 can be washed of the previous sample.

Figure 5:
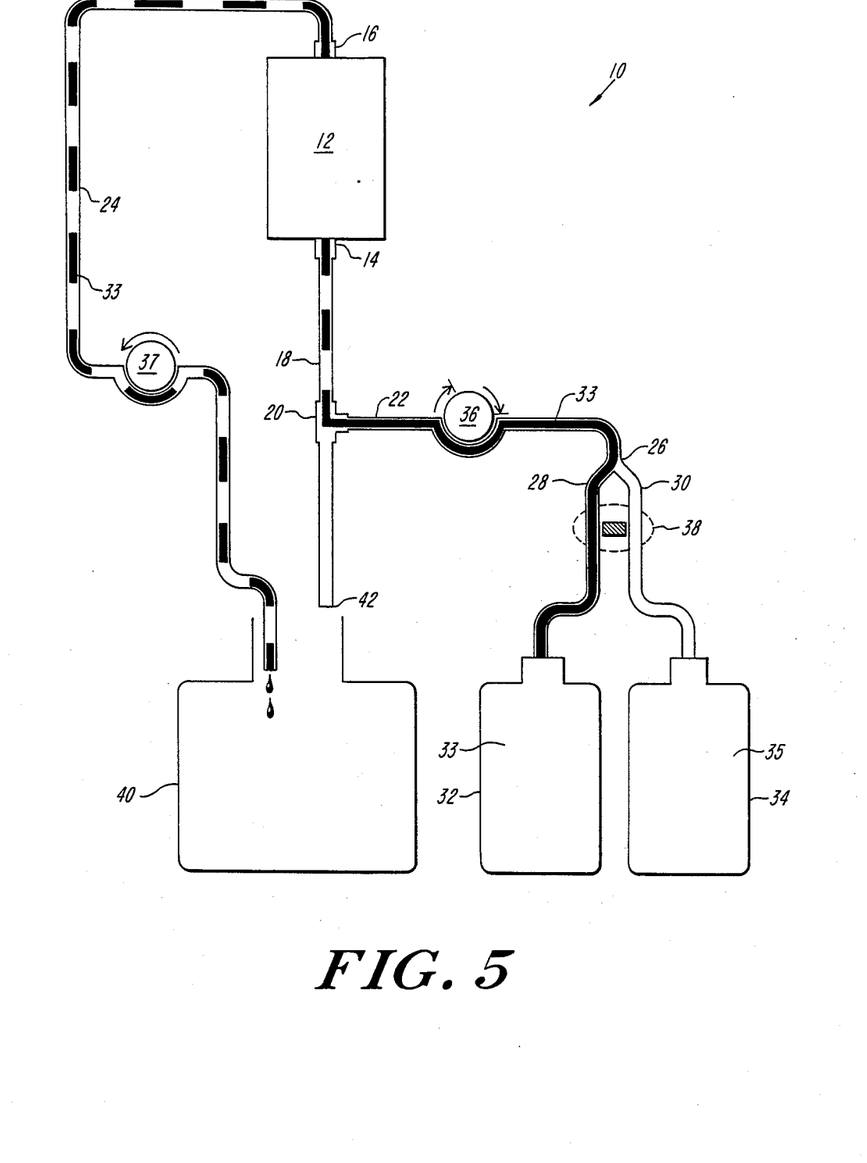
FIG. 5 is a schematic view of a second washing mode of operation of the fluid arrangement.

As illustrated in FIG. 5, in a second washing mode following the first washing mode, the second peristaltic pump 37 is started to exert a drawing force through the analyzing electrode module 12 and the first peristaltic pump 36 is operated intermittently such that second peristaltic pump 37 draws air through the sample receiving end 42 of inlet tube 18 when first peristaltic pump 36 is off, and draws first calibrant 33 through junction 20 from the fluid supply tube 22 when first peristaltic pump is on. First calibrant 33 interspersed with air pockets are drawn by the second peristaltic pump 37 through the analyzing electrode module 12 to facilitate cleaning the analyzing electrode module 12.

Figure 6:
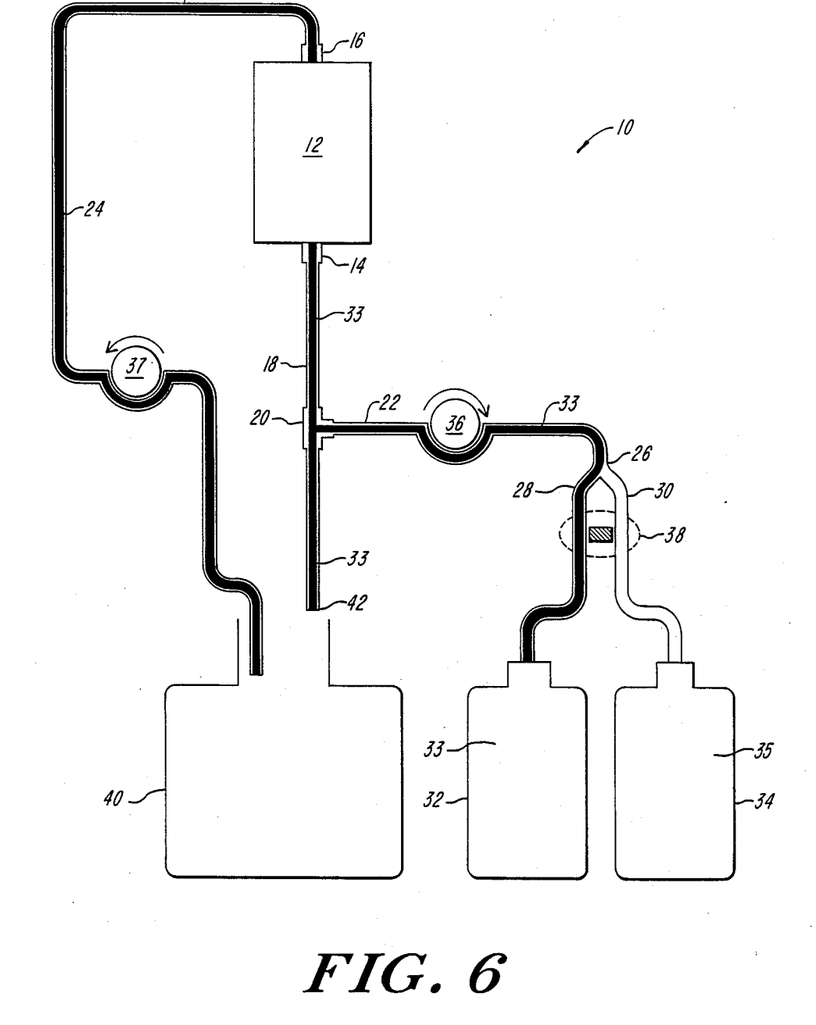
FIG. 6 is a schematic view of a calibrating mode of operation of the fluid arrangement.

Next, the system is operated in a calibrating mode as shown in FIG. 6. First peristaltic pump 36 is turned on to advance the first calibrant 33 toward the junction 20. Second peristaltic pump 37 is also turned on to advance first calibrant 33 through the outlet tube 24 toward the waste container 40. The force created by the second peristaltic pump 37 draws or aspirates first calibrant 33 entering the inlet tube 18 at the junction 20 proximally through the inlet tube 18 toward the analyzing electrode module 12. The first peristaltic pump 36 is operated at a rate approximately 10% faster than the second peristaltic pump to ensure a continuous flow of first calibrant 33 to the analyzing electrode module and prevent any air from entering the analyzing electrode module 12 at this time. The excess first calibrant 33 pumped into the junction 20 due to this difference in pump speeds passes distally away from the analyzing electrode module 12 and out the sample-receiving end 42 of the inlet tube 18. This mode allows the fluid arrangement to be filled completely with first calibrant 33 in preparation for measuring first calibrant 33 in the analyzing electrode module 12, which measurement would be distorted if there were air entering the system. Then, first peristaltic pump 36 is turned off and second peristaltic pump 37 draws the first calibrant 33 in the inlet tube 18 proximally into the analyzing electrode module 12 and the measurement occurs under the same conditions of flow as measurement of the sample fluid 46. When this measurement is completed, the first and second peristaltic pumps are turned off and the fluid arrangement is in the resting mode.

Figure 7:
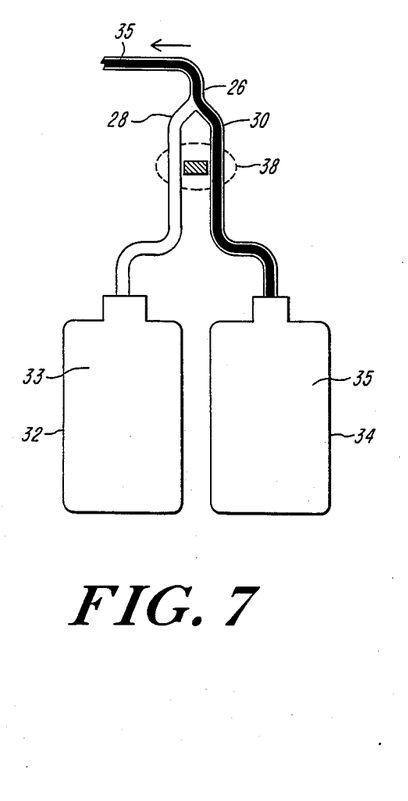
FIG. 7 is a fragmentary schematic view of a calibrating mode of the same fluid arrangement as in FIG. 6 showing a different position of a pinch valve in the arrangement.

It is further possible to operate the calibrating mode with the second calibrant 35 by reversing the pinch valve 38 to close off calibrant supply tube 28 and open calibrant supply tube 30 thereby accessing the second calibrant 35 from the second calibrant source 34. Thus, as shown in FIG. 7, the second calibrant 35 can be advanced through the fluid supply tube 22 toward the inlet tube 18. This second calibrant is introduced to ascertain the sensitivity of the analyzing module for purposes of sloping. Since changes in temperature, humidity and other variables can affect the relative measurement of the analyzing electrode module 12, this calibrating step should be performed about every four hours. This calibrating step can, of course, be carried out after each sample measurement, if desired.

As seen from the above description of the figures, the sample is introduced uncontaminated through the inlet tube 18 and into the analyzing electrode module 12 for measurement, the analyzing electrode module 12 and inlet tube 18 are washed, and the analyzing electrode module 12 measures a calibrant and is readied for the next cycle. These operations are accomplished solely by the forces created by two peristaltic pumps. There are no potentially contaminating valves necessary in this system. Furthermore, the sample fluid is measured under the same forces and conditions as the calibrants. This system has been shown to operate with high accuracy as compared with other analyzing devices. Furthermore it can be operated nearly twice as fast as certain other commercially-available analyzing devices.

As an illustration of a preferred embodiment of applicants' invention, the measurement of the potassium and sodium levels in heparinized whole blood will be described. The sample mode is initiated manually in applicants' preferred embodiment. A sampling needle is connected to the sample-receiving end 42 of the inlet tube. This needle is disposed on a cartridge that may swivel from a vertical position toward the operator. When swiveled, a switch is activated and the sampling mode begins. The second peristaltic pump 37 empties the inlet tube 18 and the analyzing electrode module 12 of first calibrant 33, replacing the calibrant with air. The first peristaltic pump is then turned in reverse direction one-quarter turn to withdraw the first calibrant 33 from the junction toward the first calibrant supply source 32. This creates an air gap 44 in the fluid supply tube 22 at the junction. Replacing the calibrant with air in the inlet tube 18 and the analyzing electrode module 12 and creating an air gap 44 in the fluid supply tube 22 takes less than two seconds.

Next the operator causes the opening of the needle to penetrate a sample of heparinized whole blood. The operator then pushes a button engaging a switch to begin the concluding steps of the cycle, all of which are automatic and controlled by a host computer. Note, however, that the concluding steps could be controlled manually although it is preferable to use computer electronics. The second peristaltic pump 37 draws a sample of whole blood from the sample reservoir through the tip of the needle. The sample in the preferred embodiment is approximately 120 microliters, although the fluid arrangement can be designed to sample as little as 50 microliters. The whole blood sample flows past the junction and into and through the electrode analyzing module. At first, the sample flows at a rate of 125 microliters per second in the most preferred embodiment of applicants' invention. The preferred range of flow speed for measuring the heparinized whole blood samples is between 75 and 200 microliters per second, although faster and slower speeds are possible. This fast flowing rate further causes a cleansing action in the analyzing electrode module. The second peristaltic pump then begins turning on and off causing a pulsatile flow and rate of about 5 microliters per second or less. In applicants' preferred embodiment, a stepper motor turning eight degrees with each pulse is employed. The sample is then analyzed at this rate. The pulsatile flow lasts for approximately four seconds. The analyzing electrode module, AMDEV 2 channel, is capable of measuring both sodium and potassium concentration and is preferred by applicants The analyzing electrode module then generates an analog signal which is converted to a digital signal by conventional electronics. This digital signal is then displayed on a liquid crystal display by the host computer. The display may, of course, be another conventional display such as a print out.

After this measurement, the computer begins the first washing mode of the fluid arrangement. The second peristaltic pump 37 is turned off and the first peristaltic pump 36 advances first calibrant 33 through the fluid supply tube 22 into the juncture 20 and distally through the inlet tube 18 and out the fluid-receiving end 42, in this case the needle attached to the fluid-receiving end. This washing mode lasts approximately one second.

Next the computer begins the second washing mode which causes air pockets and first calibrant to be alternately drawn through the analyzing electrode module. This second washing mode lasts 2-3 seconds.

The computer then starts the calibrating mode described above. After first charging the fluid arrangement with calibrant, first peristaltic pump 36 is turned off and second peristaltic pump 37 advances the calibrant in the inlet tube toward the analyzing module. The calibrant is advanced at a fast rate of 125 microliters per second at the start and then the second peristaltic pump is turned off and on to produce a pulsatile flow at a rate of about five microliters per second. This calibrating mode lasts about four seconds. As can be seen, the flow of calibrant through the analyzing electrode module occurs under exactly the same conditions as the flow of the sample through the analyzing electrode module. Note that the calibrating mode and the sample analyzing mode can be greater than four seconds or reduced to as low as one second.

At the end of the calibrating step, the computer shuts off both pumps and the system is in its resting mode. Note that in applicants' preferred embodiment, the second calibrant is introduced into the fluid arrangement in a calibrating mode automatically every four hours.

As discussed, the second peristaltic pump 37 produces a flow rate of about 125 microliters per second when it is operated continuously and the first peristaltic pump 36 is operated at a rate about ten percent faster than this. These flow rates can be adjusted relatively to flow faster or slower. Flow rate is, of course, to some extent dependent upon the tube size and the viscosity of the fluid used. In the preferred embodiment, applicants' use a tube size of 0.030 inches I.D. This tube size will accommodate heparinized whole blood at a flow rate as fast as about 200 microliters per second.

When measuring sodium and potassium levels in heparinized whole blood, applicants use a first calibrant with sodium and potassium concentrations close to the level normally existing in whole blood, that is, 140 milli-equivalents per liter of sodium and four milli-equivalents per liter of potassium. Applicants then use a second calibrant with sodium and potassium levels of 80 milli-equivalents per liter and eight milli-equivalents per liter, respectively. Although other levels may be used, applicants find that these levels work well to give reliable measurement of the sodium and potassium levels in whole blood when using the analyzing electrode module described above. Finally, the inlet tube length is minimized to increase speed and reduce the chances of contamination. In applicants' preferred embodiment, the inlet tube is straight and vertically disposed, and the length from the needle tip to the inlet port of the analyzing electrode module is approximately 2 and ¾ inches. Shorter and longer length are possible but lengths exceeding 4" begin to add substantially to the time for completing a cycle as well as increasing the likelihood of contamination.

It should be understood that various changes and modifications of the embodiment shown in the drawings may be made within the scope of this invention. Thus, one may substitute any number of analyzing electrode modules or other analyzing devices for the one described in the preferred embodiment. Likewise one may substitute other types of devices for creating the pumping and aspiration forces created by the peristaltic pumps described in the preferred embodiments. Thus, it is intended that all matter contained in the above description or shown in the accompanying drawings shall be interpreted in an illustrative and not limiting sense.

We claim:

1. In a method for analyzing fluid samples using an electrochemical measuring apparatus having an analyzing device with an inlet port and an outlet port, said outlet port connecting to an outlet tube, said inlet port connecting to an inlet tube having a sample receiving end, and said inlet tube connecting at a junction along its length to one end of a fluid supply tube having two ends, said one end and an opposite end, said fluid supply tube being connected at its opposite end to at least one fluid source, the improvement comprising a method for introducing a fluid into the inlet tube to wash said inlet tube of contaminants at the junction comprising,
    advancing the fluid from the fluid source to the junction, and
    exerting a force to move the fluid in the inlet tube at a rate that is slower than the rate the fluid advances into the junction such that a first portion of the fluid passes proximally in the inlet tube and a second portion of the fluid passes distally in the inlet tube.

2. A method as claimed in claim 1 wherein the force is characterized by continuously drawing the fluid proximally through the inlet tube at the junction, which force draws at a rate that is slower than the rate the fluid advances into the junction such that the excess fluid passes distally in the inlet tube.

3. A method as claimed in claim 2 wherein said fluid is advanced to the junction by a peristaltic pump connected at a point along the length of the fluid supply tube.

4. A method as claimed in claim 3 wherein the fluid is drawn proximally through the inlet tube by a peristaltic pump connected at a point along the length of the outlet tube.

5. A method as claimed in claim 4 wherein the analyzing device is an analyzing electrode module.

6. A method as claimed in claim 5 wherein the fluid is a calibrant.

7. A method as claimed in claim 6 wherein said apparatus is provided with a second fluid source connected to the fluid supply tube distally of the first peristaltic pump, and further comprising,
selectively closing off flow from said first or second fluid source.

8. A method as claimed in claim 7 wherein said flow is closed off by engaging or disengaging a conventional pinch valve.

9. A method as claimed in claim 4 wherein said second perstaltic pump is operated at a flow rate between 75 and 100 microliters per second.

10. In a method for analyzing fluid samples using an electrochemical measuring apparatus having an analyzing device with an inlet port and an outlet port, said outlet port connecting with an outlet tube, said inlet port connecting to an inlet tube having a sample-receiving end, and said inlet tube connecting at a junction along its length to one end of a fluid supply tube having two ends, said one end and an opposite end, which fluid supply tube is connected at its opposite end to at least one fluid source and which fluid supply tube initially is filled with fluid calibrant, the improvement comprising, a method for isolating the fluid calibrant in the fluid supply tube from fluid drawn proximally through the inlet tube past the junction and to the analyzing device by creating and maintaining an air bubble in the fluid supply tube at the junction by drawing a segment of air from said inlet tube into said fluid supply tube to isolate the fluid calibrant in the fluid supply tube from the junction,
putting the sample-receiving end of the inlet tube in contact with a fluid sample,
and exerting a force to draw the fluid sample proximally through the inlet tube.

11. A method as claimed in claim 10 wherein said bubble is created and maintained by operating a peristaltic pump disposed at a point along the length of the fluid supply tube in a manner to draw a segment of air from said inlet tube into said fluid supply tube.

12. A method as claimed in claim 11 wherein the force to draw the fluid proximally through the inlet tube is exerted by a peristaltic pump disposed at a point along the length of the outlet tube.

13. A method as claimed in claim 12 wherein the supply fluid drawn into the inlet tube passes proximally into the analyzing device.

14. In an electrochemical measuring apparatus having an analyzing device with an inlet port and an outlet port, said outlet port connecting to an outlet tube, said inlet port connecting to an inlet tube having a sample fluid receiving end, and said inlet tube connecting at a junction along its length to one end of a fluid supply tube having two ends, said one end and an opposite end, which fluid supply tube is connected at its opposite end to at least one fluid source containing a fluid, a method comprising,
causing said fluid from said supply source to flow through said fluid supply tube to said junction and causing said fluid to flow simultaneously in a proximal direction and a distal direction within the inlet tube from the junction, and
causing a fluid sample to flow through the inlet tube past the junction and into the analyzing module.

15. A method as claimed in claim 14 wherein said fluid is caused to flow simultaneously in a proximal and a distal direction by connecting a peristaltic pump at a point along the length of said fluid supply tube,
connecting a second peristaltic pump at a point along the length of said outlet tube,
and causing said first peristaltic pump to advance fluid at a faster rate than said second peristaltic pump.

16. A method as claimed in claim 15 wherein said fluid sample is drawn through said inlet tube and past the junction by causing said first peristaltic pump to create and maintain an air bubble in the fluid supply tube at the junction,
placing the sample-receiving end of the inlet tube in contact with a fluid sample source,
and causing said second peristaltic pump to exert a force to draw the sample fluid proximally through the inlet tube past the junction and into the analyzing module.

17. A method as claimed in claim 16 further comprising advancing a fluid from the fluid supply source through the fluid supply tube to the junction and then distally only through the inlet tube.

18. A method as claimed in claim 17 wherein said fluid from the fluid supply source is advanced through the fluid supply tube to the junction and then distally only through the inlet tube by operating said first peristaltic pump to advance said fluid while said second peristaltic pump is off.

19. A method as claimed in claim 18 further comprising drawing fluid through the analyzing module with intermittently spaced air bubbles to facilitate cleaning the module.

20. A method as claimed in claim 19 wherein said air bubbles are created by running said second peristaltic pump at a fixed rate and running said first peristaltic pump intermittently.

21. A method as claimed in claim 16 wherein said air bubble is created by,
operating said second peristaltic pump while said first peristaltic pump is off to draw said fluid in said inlet tube proximally past the junction and through the analyzing module to replace said fluid in said inlet tube with air, and then operating said first peristaltic pump while said second peristaltic pump is off in a manner to draw a segment of air from said inlet tube into said fluid supply tube.

22. In a method for analyzing fluid samples using an electrochemical measuring apparatus having an analyzing device with an inlet port and an outlet port, said outlet port connecting with an outlet tube, said inlet port connecting to an inlet tube having a sample-receiving end, and said inlet tube connecting at a valveless junction along its length to one end of a fluid supply tube having two ends, said one end and an opposite end, which fluid supply tube is connected at its opposite end to at least one fluid source, and said device having a first peristaltic pump disposed at a point along the length of the fluid supply tube and a second peristaltic pump disposed at a point along the length of the outlet tube, the improvement comprising, a method for introducing intermittently spaced air bubbles into the fluid at the valveless junction as the fluid passes from the fluid supply tube through the valveless junction and proximally through the inlet tube, said last mentioned method comprising,
operating said second peristaltic pump to create a continuous proximal drawing force in said inlet tube, and operating said first peristaltic pump intermittently to introduce into said inlet tube segments of fluid, said segments being spaced apart by air in the inlet tube.

23. In a method for analyzing fluid samples using an electrochemical measuring apparatus having an analyzing device with an inlet port and an outlet port, said outlet port connecting with an outlet tube, said inlet port connecting to an inlet tube having a sample-receiving end, and said inlet tube connecting at a valveless junction along its length to one end of a fluid supply tube having two ends, said one end and an opposite end, which fluid supply tube is connected at its opposite end to at least one fluid source, and said device having a first peristaltic pump disposed at a point along the length of the fluid supply tube and a second peristaltic pump disposed at a point along the length of the outlet tube, the steps comprising,
- a first step comprising operating said first peristaltic pump to advance the fluid from the fluid source to the junction and operating said second peristaltic pump to exert a force to move the fluid in the inlet tube at a rate that is slower than the rate the fluid advances into the junction such that a first portion of the fluid passes proximally in the inlet tube and a second portion of the fluid passes distally in the inlet tube,
- a second step comprising operating said second peristaltic pump while said first peristaltic pump is off to draw said fluid in said inlet tube proximally past the valveless junction and through the analyzing module to replace said fluid in said inlet tube with air and then operating said first peristaltic pump while said second peristaltic pump is off in a manner to draw a segment of air from said inlet tube into said fluid supply tube,
- a third step comprising putting the sample-receiving end of the inlet tube in contact with a fluid sample and operating said second peristaltic pump while said first peristaltic pump is off to draw the fluid sample proximally through the inlet tube past the junction and into the analyzing device,
- a fourth step comprising operating said first peristaltic pump while said second peristaltic pump is off to advance fluid from the fluid supply source through the fluid supply tube to the junction and then distally through the inlet tube to wash the inlet tube, and
- a fifth step comprising operating said second peristaltic pump to create a continuous proximal drawing force in said inlet tube and operating said first peristaltic pump intermittently to introduce into said inlet tube segments of fluid, said segments being spaced apart by air in the inlet tube for washing the analyzing device.

* * * * *